(12) United States Patent
Zhao

(10) Patent No.: US 11,224,333 B2
(45) Date of Patent: Jan. 18, 2022

(54) STEREO ENDOSCOPE

(71) Applicant: OLYMPUS WINTER & IBE GMBH, Hamburg (DE)

(72) Inventor: Jianxin Zhao, Hamburg (DE)

(73) Assignee: OLYMPUS WINTER & IBE GMBH, Hamburg (DE)

(*) Notice: Subject to any disclaimer, the term of this patent is extended or adjusted under 35 U.S.C. 154(b) by 58 days.

(21) Appl. No.: 16/754,176

(22) PCT Filed: Oct. 1, 2018

(86) PCT No.: PCT/EP2018/076668
§ 371 (c)(1),
(2) Date: Apr. 7, 2020

(87) PCT Pub. No.: WO2019/072615
PCT Pub. Date: Apr. 18, 2019

(65) Prior Publication Data
US 2021/0219825 A1    Jul. 22, 2021

(30) Foreign Application Priority Data
Oct. 9, 2017 (DE) .................. 10 2017 123 320.2

(51) Int. Cl.
*G02B 23/24* (2006.01)
*A61B 1/00* (2006.01)
*A61B 1/05* (2006.01)

(52) U.S. Cl.
CPC ...... *A61B 1/00193* (2013.01); *A61B 1/00096* (2013.01); *A61B 1/00179* (2013.01); *A61B 1/05* (2013.01)

(58) Field of Classification Search
CPC ............ A61B 1/00193; A61B 1/00179; A61B 1/00096; A61B 1/05
See application file for complete search history.

(56) References Cited

U.S. PATENT DOCUMENTS 4,832,003 A * 5/1989 Yabe ............... A61B 1/051
348/65
5,005,957 A * 4/1991 Kanamori ........ G02B 13/18
359/663

(Continued)

FOREIGN PATENT DOCUMENTS

DE        195 32 400 A1    3/1996
DE    20 2012 004 290 U1    5/2012

(Continued)

OTHER PUBLICATIONS

German Office Action dated Jun. 28, 2018 received in DE 10 2017 123 320.2.

(Continued)

*Primary Examiner* — Aaron B Fairchild
*Assistant Examiner* — Shankar Raj Ghimire
(74) *Attorney, Agent, or Firm* — Scully, Scott, Murphy & Presser, P.C.

(57) ABSTRACT

A stereo endoscope including: a shaft; and an objective lens including: a distal objective lens portion, where beam paths of right and left partial images extend through common optical components; a proximal objective lens portion, where the beam paths of the right and left partial images extend through separate optical components; and a transition portion, where the beam paths of the right and left partial images, which emerge from the distal objective lens portion at an angle to one another, are aligned parallel to one another; the transition portion comprises a lateral spreading arrangement including optical components for increasing a distance between the beam paths of the right and left partial images; and the lateral spreading arrangement is configured to laterally spread the beam paths of the right and left partial images asymmetrically in relation to an optical axis of the distal objective lens portion.

10 Claims, 4 Drawing Sheets

(56) References Cited

U.S. PATENT DOCUMENTS

| | | | |
|---|---|---|---|
| 5,095,887 A | | 3/1992 | Leon et al. |
| 5,327,283 A | * | 7/1994 | Zobel .................. G02B 23/243 |
| | | | 359/434 |
| 5,459,605 A | * | 10/1995 | Kempf ................ A61B 1/00165 |
| | | | 359/462 |
| 5,588,948 A | * | 12/1996 | Takahashi .............. A61B 1/042 |
| | | | 600/111 |
| 5,689,365 A | * | 11/1997 | Takahashi .............. G02B 23/24 |
| | | | 359/362 |
| 5,743,846 A | * | 4/1998 | Takahashi .......... A61B 1/00193 |
| | | | 600/111 |
| 5,912,763 A | * | 6/1999 | Spink .................... G02B 21/22 |
| | | | 359/363 |
| 6,104,426 A | * | 8/2000 | Street ................ G02B 23/2415 |
| | | | 348/45 |
| 6,256,155 B1 | * | 7/2001 | Nagaoka ................ G02B 13/04 |
| | | | 359/726 |
| 10,088,665 B2 | * | 10/2018 | Zhao .................... G02B 23/243 |
| 10,698,194 B2 | * | 6/2020 | Zhao ................. G02B 23/2415 |
| 2002/0114231 A1 | * | 8/2002 | Shirakawa ........... G11B 7/1369 |
| | | | 369/44.32 |
| 2006/0146325 A1 | * | 7/2006 | Wachsmuth .............. G01J 3/36 |
| | | | 356/318 |
| 2007/0047073 A1 | | 3/2007 | Zimmer et al. |
| 2015/0043065 A1 | * | 2/2015 | Hong .................... G02B 21/22 |
| | | | 359/376 |
| 2016/0154231 A1 | * | 6/2016 | Zhao ................. A61B 1/00193 |
| | | | 348/45 |
| 2017/0112369 A1 | | 4/2017 | Czupalla et al. |
| 2017/0202439 A1 | * | 7/2017 | Wu ........................ A61B 1/313 |
| 2018/0180868 A1 | | 6/2018 | Zhao |
| 2021/0219825 A1 | * | 7/2021 | Zhao ................. A61B 1/00179 |

FOREIGN PATENT DOCUMENTS

| | | |
|---|---|---|
| DE | 10 2013 215 422 A1 | 2/2015 |
| DE | 10 2013 217 449 A1 | 3/2015 |
| DE | 10 2015 217 079 B4 | 3/2017 |
| DE | 10 2015 118 199 A1 | 4/2017 |
| EP | 3 037 864 A2 | 6/2016 |
| WO | 2019/072615 A1 | 4/2019 |

OTHER PUBLICATIONS

International Search Report dated Jan. 9, 2019 received in PCT/EP2018/076668.

* cited by examiner

STEREO ENDOSCOPE

CROSS-REFERENCE TO RELATED APPLICATION

The present application is based upon and claims the benefit of priority from PCT/EP2018/076668 filed on Oct. 1, 2018, which claims benefit to DE 10 2017 123 320.2 filed on Oct. 9, 2017, the entire contents of each of which are incorporated herein by reference.

BACKGROUND

Field

The present disclosure relates to a stereo endoscope and more particularly to a stereo endoscope comprising a shaft and an objective disposed at the distal end of the shaft, wherein the objective lens comprises the following: a distal objective lens portion, in which beam paths of a right partial image and of a left partial image extend through common optical components; a proximal objective lens portion, in which the beam paths of the right partial image and of the left partial image extend through separate optical components; and a transition portion, in which the beam paths of the right partial image and of the left partial image, which emerge from the distal objective lens portion at an angle to one another, are aligned parallel to one another; and wherein the transition portion comprises a lateral spreading arrangement in order to increase the distance between the beam paths of the right partial image and of the left partial image.

Prior Art

Endoscopes are used to view regions that are hard to access, for example body cavities of a human or animal patient or the interior of technical installations. To this end, they have a narrow shaft which is introduced into the cavity of interest through an opening that is either present or produced for the examination. An objective lens for receiving an image of objects situated in the cavity is situated at the distal end of the shaft.

For some time now, use has increasingly been made of stereo endoscopes, i.e., endoscopes that record two partial images under slightly deviating viewing angles. Using suitable technical means, these partial images are then presented in such a way that a user perceives a three-dimensional image of an observed object.

The objective lens of stereo endoscopes usually comprises a distal objective lens portion, in which beams of a right partial image and of a left partial image propagate through common optical components. This design allows the optical components of the distal objective lens portion to be manufactured with a large diameter, which is required for high image resolution, particularly in the case of a large aperture angle.

The beams of the right partial image and of the left partial image emerge from the distal objective lens portion at an angle to one another. Since, from a technical point of view, a parallel propagation is easier to realize for the transmission of the beams, the distal objective lens portion is followed by a transition portion, in which the beams are aligned parallel to one another. To this end, the transition portion usually comprises a positive lens.

The beams of the right partial image and of the left partial image, now propagating parallel to one another, are now imaged to form the respective partial images in a proximal objective lens portion. In the proximal objective lens portion, the beams of the right partial image and of the left partial image propagate through separate optical components.

A corresponding objective lens is described in DE102013215422A1.

The achievable spacing of the optical axes of the two beams in the proximal objective lens portion is relatively small, and so only optical components with a small diameter can be used in this objective lens portion. This restricts the achievable image quality. In order to take remedial action here, there have been the occasional propositions to laterally spread the two beams. Here, the beams are deflected in opposite directions through 90° within the scope of a first reflection and then steered back into the initial direction in a second reflection through 90°.

In order to avoid trimming of the beams in the two reflections, each beam must be offset to one side at least by a distance that approximately corresponds to the diameter of the beam. However, the resultant minimum lateral spread is often greater than what would be required for placing the optical components of the proximal objective lens portion. However, a lateral spread going beyond the dimension required to this end increases the installation space required for the objective lens, and is therefore disadvantageous.

FIG. 2 illustrates an objective lens 100 of a stereo endoscope of the prior art. The objective lens 100 comprises a distal objective lens portion A, a transition portion B and a proximal objective lens portion C.

In the illustrated example, the distal objective lens portion A comprises only a single diverging lens 101. The transition portion B comprises a converging lens 102 and a stop 103 with apertures 104, 105 for a beam of the right partial image and a beam of the left partial image.

The transition portion B is adjoined by the proximal objective lens portion C, which comprises two lens systems 106, 107 that are disposed parallel to one another. Image recorders 108, 109, such as image sensors, convert the images imaged by the objective 100 into electrical signals for further processing. At the distal side, the objective lens 100 is closed off by a window 110.

The path of the beams of the right partial image and of the left partial image is indicated by two light rays 111, 112, which propagate along the optical axes of the lens systems 106, 107.

FIG. 3 illustrates an objective lens 200. In many aspects, the objective lens corresponds to the objective lens 100 from FIG. 2; corresponding components are therefore provided with reference signs whose numerical value has increased by 100 and are not described again.

In contrast to the objective lens 100 of FIG. 2, the transition portion B of the objective lens 200 comprises a lateral spreading arrangement made of two rhomboid prisms 220, 221, which laterally spread the beams of the right partial image and of the left partial image apart by twofold reflection, as is evident from the path of the rays 211, 212.

The rhomboid prisms 220, 221 must laterally offset the beams by at least a distance that corresponds to the diameter of the beams and consequently to approximately the diameter of the apertures 204, 205. It is evident that the lens systems 206, 207 are pulled very far apart on account of this significant lateral spread, and so the objective lens 200 requires very much installation space in the proximal portion.

SUMMARY

It is therefore an object to provide a stereo endoscope whose objective lens is improved in respect of the above-described problem.

Accordingly, such object can be achieved by a stereo endoscope comprising a shaft and an objective lens disposed at the distal end of the shaft, wherein the objective lens comprises the following: a distal objective lens portion, in which beam paths of a right partial image and of a left partial image extend through common optical components; a proximal objective lens portion, in which the beam paths of the right partial image and of the left partial image extend through separate optical components; and a transition portion, in which the beam paths of the right partial image and of the left partial image, which emerge from the distal objective lens portion at an angle to one another, are aligned parallel to one another; and wherein the transition portion comprises a lateral spreading arrangement in order to increase the distance between the beam paths of the right partial image and of the left partial image; and which is developed in that the lateral spreading arrangement is configured to laterally spread the beam paths of the right partial image and of the left partial image in asymmetric fashion in relation to an optical axis of the distal objective lens portion. An asymmetric lateral spread is understood to mean a lateral spread in which one of the two beams is offset to the side by a first distance and in which the other beam is not offset to the side, or is offset to the side by a second distance that is shorter than the first distance.

As a result of this embodiment of the lateral spreading arrangement, it is possible to obtain a sufficient lateral spread of the beam paths without unnecessarily increasing the installation space required for the objective lens.

In one embodiment, the lateral spreading arrangement can comprise a first prism arrangement, in which one of the beam paths of the right partial image or of the left partial image is offset in parallel by way of multiple reflections. By way of example, the prism arrangement may comprise two half-cube prisms or a rhomboid prism.

The lateral spreading arrangement can comprise a plane glass element, through which the beam path not extending through the first prism arrangement extends. This can compensate for the longer beam path through the prism arrangement such that both beams traverse approximately the same optical path length. Here, the optical path length through the plane glass element can approximately correspond to the optical path length through the first prism arrangement.

In an embodiment, the distal objective lens portion can comprise a second prism arrangement for bending a direction of view of the stereo endoscope.

Stereo endoscopes are offered with different directions of view. Here, as a rule, an angle between the direction of view of the stereo endoscope and a longitudinal axis of the stereo endoscope is specified for the purposes of specifying the direction of view. While stereo endoscopes looking straight ahead with a direction of view of 0° have a simpler construction, stereo endoscopes with a direction of view deviating from 0° are better suited to many applications since, in this case, a rotation of the stereo endoscope about the longitudinal axis of the shaft allows a larger area to be examined.

In an embodiment of a stereo endoscope, the distal objective lens portion and the proximal objective lens portion can be configured to be rotatable against one another about the optical axis of the distal objective lens portion. As a result, the distal objective lens portion with the second prism arrangement can be rotated and consequently the direction of the view of the stereo endoscope can be changed without changing a horizontal alignment of the recorded image, which is set by the position of the proximal objective lens portion.

In an embodiment, the stereo endoscope can be a video stereo endoscope and each of the right partial image and the left partial image is imaged on a separate image recorder. Here, at least one of the two image recorders can be aligned parallel to a longitudinal axis of the stereo endoscope.

The installation space required for the image recorders can be further reduced by an appropriate alignment of one or both image recorders. Here, an alignment parallel to a longitudinal axis of the stereo endoscope is understood to mean an alignment of the image recorder or recorders, in which an image plane of the image recorder or recorders extends parallel to the longitudinal axis of the video endoscope. Such an alignment is also referred to as a horizontal alignment.

To this end, the proximal objective lens portion of a stereo endoscope can comprise at least one third prism arrangement, by means of which the beam path of the left partial image and/or the beam path of the right partial image is deflected through 90°.

BRIEF DESCRIPTION OF THE DRAWINGS

The embodiments are explained in more detail below on the basis of a few exemplary representations. In detail.

DETAILED DESCRIPTION

Figure 1:
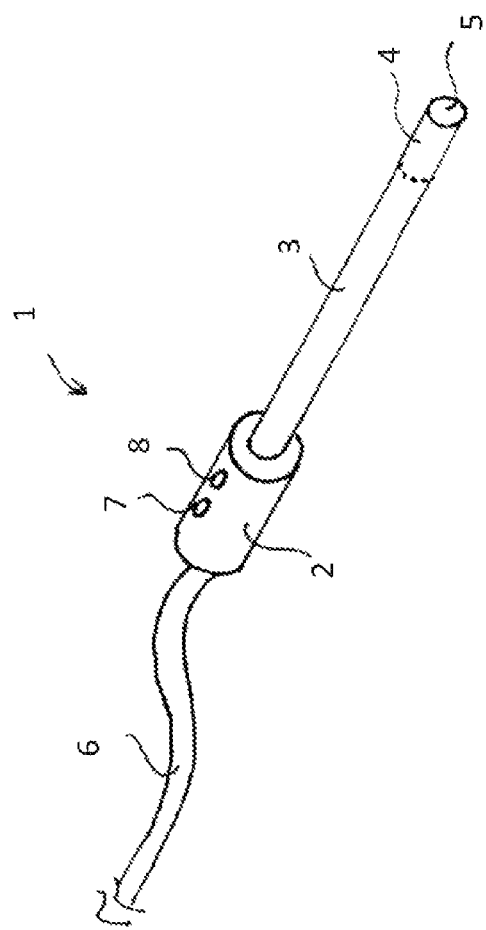
FIG. 1 illustrates a stereo endoscope.
Figure 2:
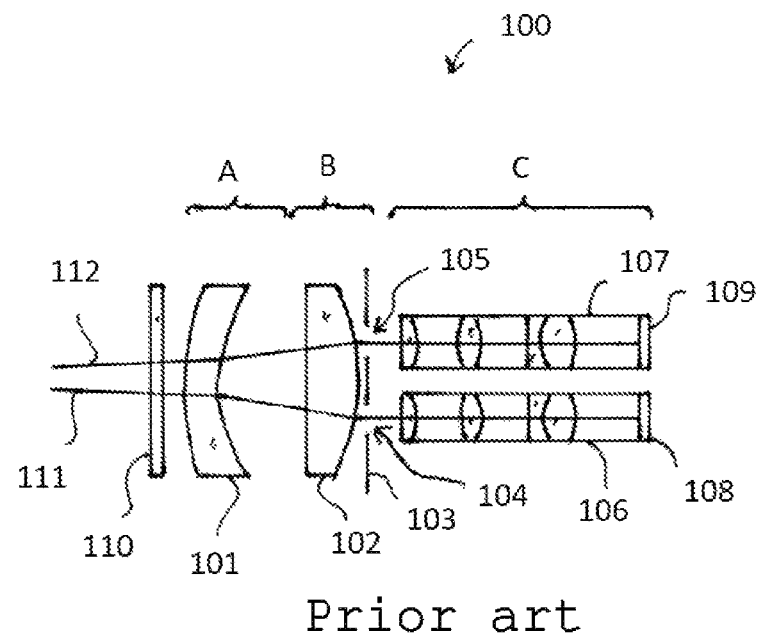
FIG. 2 illustrates an objective lens of a stereo endoscope according to the prior art.
Figure 3:
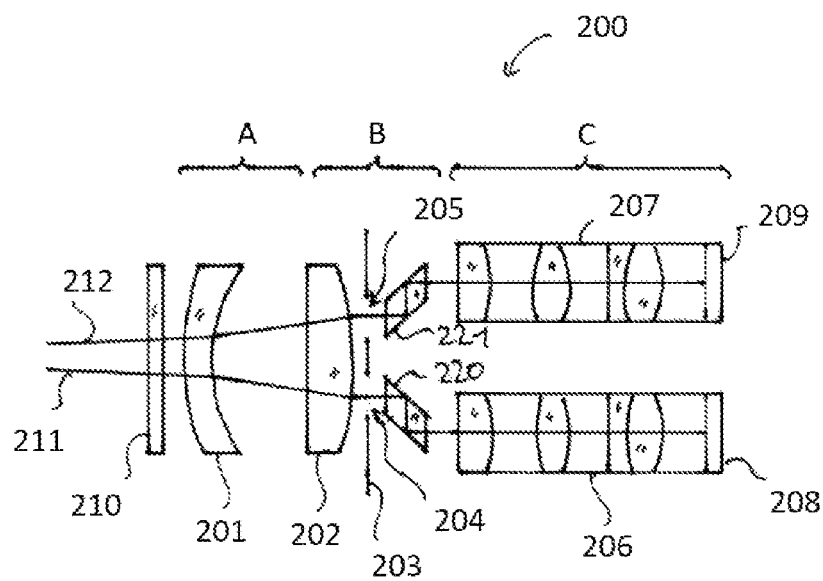
FIG. 3 illustrates an objective lens of a further stereo endoscope according to the prior art.

FIG. 1 shows a stereo endoscope 1 with a main body 2 and an elongate shaft 3. An objective lens 4 is disposed in the distal portion of the shaft 3. At the distal end, the shaft 3 is closed off by a window 5.

A supply and signal cable 6 serves to connect the stereo endoscope 1 to a light source, not illustrated here, and an image processing device, likewise not illustrated here.

Finger switches 7, 8 are provided at the main body 2 of the stereo endoscope 1, the stereo endoscope 1 and, optionally, the light source and/or the image processing device being able to be controlled by way of said finger switches.

Figure 4:
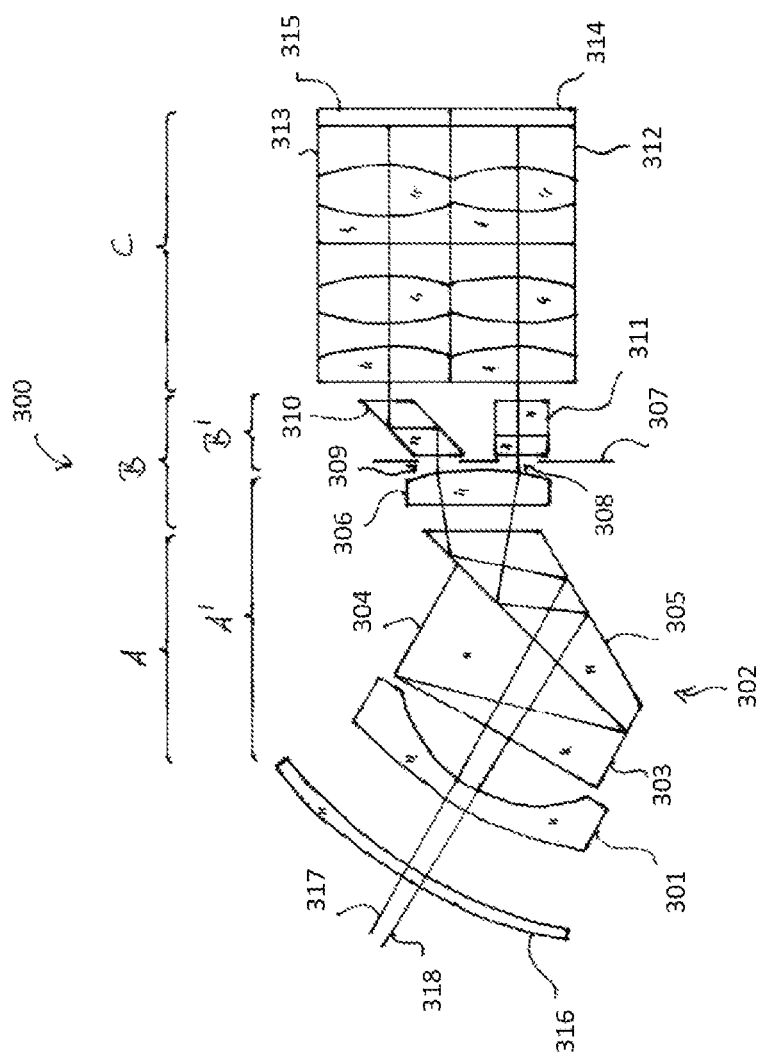
FIG. 4 illustrates an objective lens of a stereo endoscope.

FIG. 4 illustrates an objective lens 300 of a stereo endoscope, which is presented in accordance with one embodiment.

The objective lens 300 once again comprises a distal objective lens portion A, a transition portion B and a proximal objective lens portion C. The distal objective lens portion A comprises a diverging lens 301 and a prism arrangement 302 made of three prisms 303, 304, 305, by means of which the direction of view of the stereo endoscope is deflected.

The transition portion B comprises a converging lens 306 and a stop 307 with apertures 308, 309 for the beams of the right and of the left partial image. Furthermore, the transition portion B comprises an asymmetric lateral spreading arrangement comprising a rhomboid prism 310 and a plane glass block 311. While the rhomboid prism 310 laterally offsets the beam of one partial image by way of multiple reflections, the other beam propagates through the plane glass block 311 in a straight line. Here, the optical path length of both beams remains approximately the same. To this end, the plane glass block 311 may be produced from one or more glass materials that have a higher refractive index than the material of the rhomboid prism 310.

Once again, the proximal objective portion C comprises two parallel lens systems 312, 313, image recorders 314, 315, such as image sensors, being disposed at the proximal end thereof.

The objective lens 300 is closed off by a window 316, which is embodied as a spherically curved window in the present example.

The path of the beams of the two partial images is indicated by the rays 317, 318.

For the purposes of changing the direction of view of the objective 300, the distal objective lens portion A can be rotated in relation to the proximal objective lens portion C. As a result, the direction of view rotates about a longitudinal axis of the stereo endoscope. Here, the axis of rotation is located in the central axis of the converging lens 306. During the rotation, the transition portion B, in the entirety thereof, or only the stop 307 remains stationary with respect to the proximal objective lens portion C.

The division of the objective lens portions A, B, C is guided by the function of the respective optical components of the portions. In the case of a structural implementation of an objective lens, the optical components can be combined into groups that deviate from the specified objective lens portions A, B, C. By way of example, the components 301, 303, 304, 305, illustrated in FIG. 4, of the objective lens portion A can be combined together with the components 306 of the objective lens portion B to form a distal objective lens group A', while a transition group B' only comprises the components 307, 310, 311. Other combinations of the components to form groups are likewise conceivable and possible.

Figure 5A:
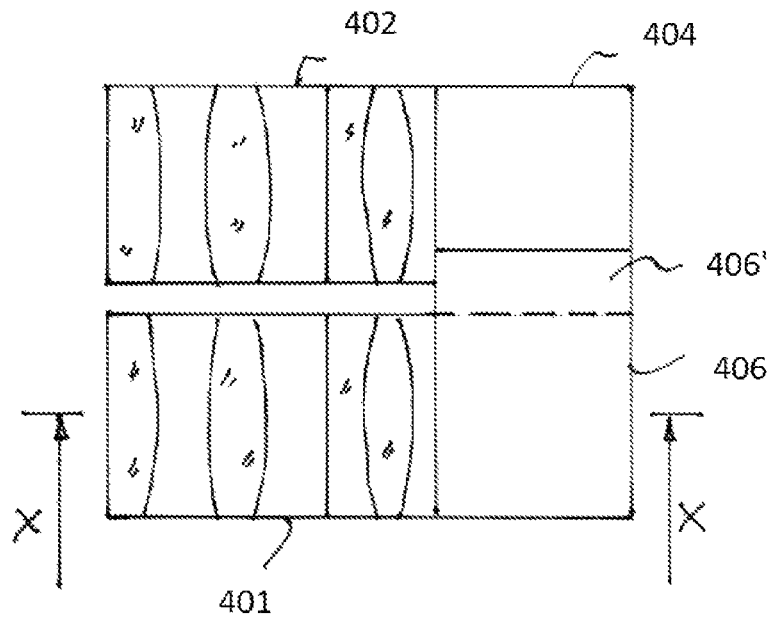
FIG. 5 illustrates an objective lens of a further stereo endoscope.
Figure 5B:
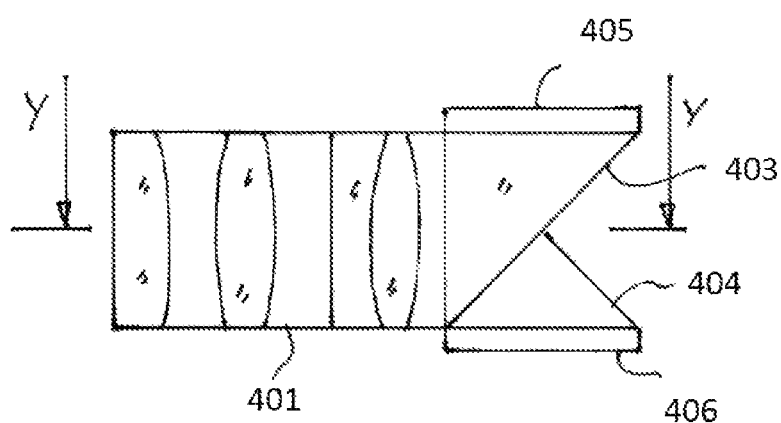

FIGS. 5a and 5b illustrate a proximal objective lens portion of a variant of a stereo endoscope in two views. The remaining objective lens portions are embodied in accordance with FIG. 4 and not illustrated for the purposes of an improved overview.

FIG. 5a shows a view from a direction that extends perpendicular to the horizontal plane of the objective lens and that is indicated by the arrows Y in FIG. 5b. FIG. 5b shows a view from a direction that extends parallel to the horizontal plane of the objective lens and that is indicated in FIG. 5a by the arrows X.

The proximal objective lens portion consists of two parallel lens systems 401, 402, of which only the lens system 401 is visible in FIG. 5b. Unlike what is illustrated in FIG. 4, the lens systems 401, 402 are each adjoined by a half cube prism 403, 404, which deflects a beam propagating through the respective lens system 401, 402 through 90° by way of reflection. Image recorders 405, 406 are disposed at the exit side of the half cube prisms 403, 404.

In FIG. 5a, the half cube prism 403 is covered by the image recorder 405. The image recorder 406 is covered by the half cube prism 404.

The image recorders 405, 406 can be attached in particularly space-saving fashion in the arrangement according to FIGS. 5a, 5b. In particular, a light-sensitive element-free control portion 406' of the image recorder 406 is aligned in such a way that it requires little space. A corresponding control portion of the image recorder 405, which is not visible in FIGS. 5a, 5b, has a corresponding alignment.

The embodiments illustrated in the Figures merely serve as examples and can be modified and/or combined among themselves. Thus, for example, the embodiment illustrated in FIG. 4 can be embodied with a direction of view that extends parallel to the longitudinal axis of the stereo endoscope when a prism arrangement 302 is dispensed with. As an alternative or in addition thereto, the window 316 can be embodied as a plane window. Likewise, the illustrated lens systems may be embodied with different numbers, types and/or combinations of optical elements.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A stereo endoscope comprising:
   a shaft; and
   an objective lens disposed at the distal end of the shaft;
      wherein the objective lens comprises:
      a distal objective lens portion in which beam paths of a right partial image and of a left partial image extend through one or more common optical components;
      a proximal objective lens portion in which the beam paths of the right partial image and of the left partial image extend through first and second separate optical components; and
      a transition portion, in which the beam paths of the right partial image and of the left partial image, which emerge from the distal objective lens portion at an angle to one another, are aligned parallel to one another;
   wherein the transition portion comprises a lateral spreading arrangement comprising first and second optical components for increasing a distance between the beam paths of the right partial image and of the left partial image, respectively; and
   one of the first and second optical components is configured to laterally offset the beam path of the corresponding right or left partial image to a greater extent than the other of the first and second optical components laterally offsets the beam path of the corresponding right or left partial image.

2. The stereo endoscope as claimed in claim 1, wherein the one of the first and second optical components of the lateral spreading arrangement comprises a prism, in which the beam path of the corresponding right or left partial image is laterally offset by way of multiple reflections.

3. The stereo endoscope as claimed in claim 2, wherein the other of the first and second optical components of the lateral spreading arrangement comprises a plane glass element, in which the beam path of the corresponding right or left partial image is not laterally offset.

4. The stereo endoscope as claimed in claim 3, wherein an optical path length through the plane glass element approximately corresponds to an optical path length through the prism.

5. The stereo endoscope as claimed in claim 1, wherein the distal objective lens portion comprises a prism for bending a direction of view of the stereo endoscope.

6. The stereo endoscope as claimed in claim 5, wherein the distal objective lens portion and the proximal objective lens portion are configured to be rotatable against one another about the optical axis of the distal objective lens portion.

7. The stereo endoscope as claimed in claim 1, further comprising first and second image sensors configured to image the right partial image and the left partial image, respectively.

8. The stereo endoscope as claimed in claim 7, wherein at least one of the first and second image sensors is aligned parallel to a longitudinal axis of the stereo endoscope.

9. The stereo endoscope as claimed in claim 7, wherein the proximal objective lens portion comprises at least one prism configured to deflect one or more of the beam path of the left partial image and the beam path of the right partial image through 90°.

10. A stereo endoscope comprising:
   a shaft; and
   an objective lens disposed at the distal end of the shaft;
   wherein the objective lens comprises:
      a distal objective lens portion in which beam paths of a right partial image and of a left partial image extend through one or more common optical components;
      a proximal objective lens portion in which the beam paths of the right partial image and of the left partial image extend through first and second separate optical components; and
      a transition portion, in which the beam paths of the right partial image and of the left partial image, which emerge from the distal objective lens portion at an angle to one another, are aligned parallel to one another;
   wherein the transition portion comprises a lateral spreading arrangement comprising two or more optical components for increasing a distance between the beam paths of the right partial image and of the left partial image;
   the lateral spreading arrangement is configured to laterally spread the beam paths of the right partial image and of the left partial image asymmetrically in relation to a central optical axis of the objective lens;
   one of the two or more optical components of the lateral spreading arrangement comprises a first prism, in which one of the beam paths of the corresponding right partial image or of the left partial image is offset in parallel by way of multiple reflections;
   an other of the two or more optical components of the lateral spreading arrangement comprises a plane glass element, through which the beam path not extending through the first prism extends; and
   an optical path length through the plane glass element approximately corresponds to an optical path length through the first prism.

* * * * *